(12) United States Patent
Moriya et al.

(10) Patent No.: US 7,760,356 B2
(45) Date of Patent: Jul. 20, 2010

(54) OPTICAL MEASURING DEVICE AND METHOD, AND NANOPARTICLE MEASURING METHOD AND DEVICE

(75) Inventors: Naoji Moriya, Kyoto (JP); Shinichro Totoki, Kyoto (JP); Yuzo Nagumo, Kyoto (JP); Yukihisa Wada, Kyoto (JP); Naofumi Sakauchi, Kyoto (JP); Fujio Inoue, Kyoto (JP); Masahiro Takebe, Kyoto (JP); Makiko Masutomi, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 39 days.

(21) Appl. No.: 11/661,492

(22) PCT Filed: Jul. 15, 2005

(86) PCT No.: PCT/JP2005/013189

§ 371 (c)(1),
(2), (4) Date: Nov. 13, 2007

(87) PCT Pub. No.: WO2006/025158

PCT Pub. Date: Mar. 9, 2006

(65) Prior Publication Data

US 2008/0192252 A1    Aug. 14, 2008

(30) Foreign Application Priority Data

Aug. 30, 2004  (JP) ............... 2004-250589
Sep. 14, 2004  (JP) ............... 2004-266768

(51) Int. Cl.
*G01N 15/02*  (2006.01)
(52) U.S. Cl. ............ 356/336; 356/338; 356/342
(58) Field of Classification Search ......... 356/336–338, 356/342–344
See application file for complete search history.

(56) References Cited

U.S. PATENT DOCUMENTS 5,215,883 A   6/1993   Chu
5,479,256 A   12/1995  Tamai et al.
(Continued)

FOREIGN PATENT DOCUMENTS

JP    3396241    2/2003
(Continued)

OTHER PUBLICATIONS

International Search Report for International Application No. PCT/JP2005/013189 dated Oct. 25, 2005.

*Primary Examiner*—Gregory J Toatley, Jr.
*Assistant Examiner*—Iyabo S Alli
(74) *Attorney, Agent, or Firm*—Cheng Law Group, PLLC

(57) ABSTRACT

The invention provides an optical measuring device capable of performing measuring using a transient diffraction grating by only adjusting probe light, and a nanoparticle measuring device using the same principle as the optical measuring device. An optical measuring device includes: a power supply 15; a container 11 that stores a sample; a pair of electrodes 13 and 14 that generate an electric force line distribution in which areas having high electric force line density and areas having low electric force line density are regularly arranged; a dielectrophoresis control unit 19 that controls the generation of a transient diffraction grating using dielectrophoresis of particles in the sample caused by applying the voltage to the pair of electrodes 13 and 14 and a variation in the transient diffraction grating due to the diffusion of the particles in the sample according to a variation in the applied voltage; a light source 16 emitting light to the transient diffraction grating; and a plurality of photodetectors 18 detecting diffracted light generated by the transient diffraction grating. In the optical measuring device, the particles are evaluated on the basis of a variation in the intensity of the diffracted light generated by the transient diffraction grating. Further, for example, the particle diameter of a nanoparticle is measured by the same principle as the optical measuring device uses. As a result, it is possible to increase the intensity of a signal and to improve the sensitivity and the S/N ratio, as compared to a dynamic scattering method.

14 Claims, 12 Drawing Sheets

U.S. PATENT DOCUMENTS

| | | | | |
|---|---|---|---|---|
| 5,484,571 | A * | 1/1996 | Pentoney et al. | 356/318 |
| 6,753,047 | B1 * | 6/2004 | Athey | 359/580 |
| 2004/0224380 | A1 * | 11/2004 | Chou et al. | 435/29 |
| 2005/0045821 | A1 * | 3/2005 | Noji et al. | 250/311 |

FOREIGN PATENT DOCUMENTS

| | | |
|---|---|---|
| JP | 2004-085528 | 3/2004 |
| WO | WO-92/00796 | 1/1992 |

* cited by examiner

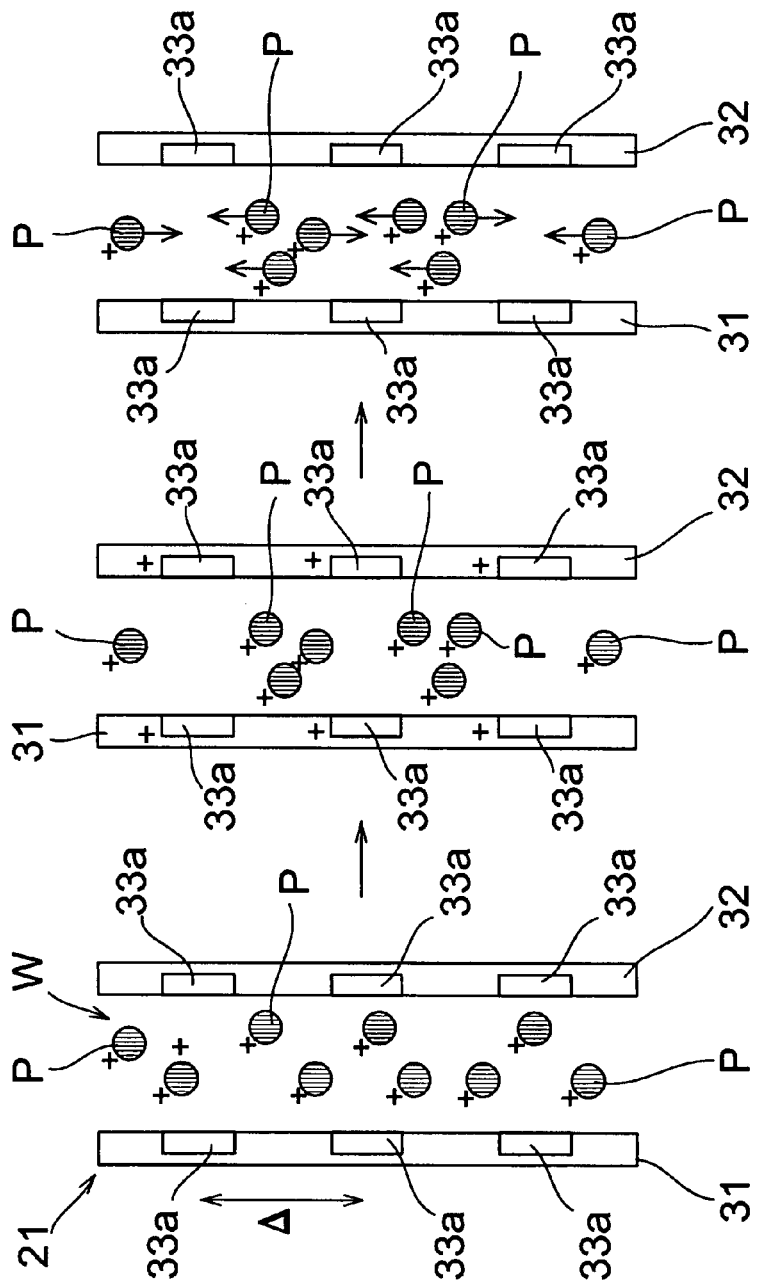

OPTICAL MEASURING DEVICE AND METHOD, AND NANOPARTICLE MEASURING METHOD AND DEVICE

TECHNICAL FIELD

The present invention relates to an optical measuring device and method for measuring information on diffusion of particles present within a liquid (biomolecules of, for example, protein and various minute particles) by using light diffracted by a transient diffraction grating generated by the particles and to a method and device for measuring diameters of nanoparticles whose diameters are equal to or less than 100 nm by using the same principle as the optical measuring device and method.

The methods and devices according to the invention can be applied to research and study for molecules in the fields of, for example, drug discovery, biotechnology, and food. Also, the methods and devices according to the invention can be applied to a particle measurement field in which the diameters of particles are measured by measuring diffusion coefficients.

BACKGROUND ART

There is a transient diffraction grating method as one of methods of measuring diffusion of particles. For example, a method for measuring a diffusion constant by means of the transient diffraction grating method, thereby detecting protein association based upon a change of the diffusion constant has been disclosed (see Japanese Patent Laid-Open Publication No. 2004-85528).

According to the transient diffraction grating method according to the related art, as shown in FIG. 6, two pulse excitation light beams with the same wavelength are radiated onto a sample such that the beams cross each other, thereby forming interference fringes. While molecules (particles) in the sample present in bright portions of the interference fringes formed by the pulse excitation light beams are partially photoexcited, molecules (particles) in the sample present in dark portions of the interference fringes are not photoexcited. Therefore, the photoexcited molecules and the non-photoexcited molecules are alternately present in a regular arrangement in an area where the interference fringes are formed, and a diffraction grating (transient diffraction grating) is temporarily generated in their diffusion process.

When a probe light beam is additionally radiated to the area where the transient diffraction grating is formed, the probe light beam is diffracted by the transient diffraction grating. After the transient diffraction grating is formed of the photoexcited molecules and the non-photoexcited molecules by emitting pulse excitation light, as time goes on, the photoexcited molecules and the non-photoexcited molecules are diffused to be mixed together, so that the transient diffraction grating vanishes. Then, the intensity of the diffracted light beam of the probe light beam generated from the transient diffraction grating decays. The decay curve of the intensity of the diffracted light beam at that time represents a diffusion constant (diffusion coefficient) of the molecules in the sample, and it is thus possible to calculate the diffusion coefficient of the molecules in the sample based upon the decay curve, and to further obtain information on the size (particle diameter), the shape, and interaction with a solvent of each of the particles in the sample based upon the diffusion coefficient.

Particles whose diameters are equal to or less than 100 nm are generally referred to as nanoparticles. Also, nanoparticles have different properties from the bulk materials of the same molecules. For these reasons, nanoparticles have been used in various fields. Various methods of measuring the diameters of particles including a laser diffraction/scattering method have been known. However, in order to measure the diameters of nanoparticles whose diameters are equal to or less than 100 nm, mainly, methods based on a measuring method referred to as a dynamic scattering method (photon correlation method) have been used (for example, U.S. Pat. No. 5,094,532 and Japanese Patent Laid-Open Publication No. 2001-159595).

The dynamic scattering method uses Brownian motion of particles. In the dynamic scattering method, a light beam is radiated to particles undergoing Brownian motion in a medium and the intensity of the light beam scattered by the particles is measured at a predetermined position, so that a fluctuation in the intensity of the scattered light beam variation in the scattered light over time, which is caused by the Brownian motion of the particles, is caught. Also, the distribution of the particles of a particle group to be measured is calculated by using the fact that each particle undergoes the Brownian motion with an intensity based on its diameter.

[Patent Document 1] Japanese Patent Laid-Open Publication No. 2004-85528
[Patent Document 2] U.S. Pat. No. 5,094,532
[Patent Document 3] Japanese Patent Laid-Open Publication No. 2001-159595

DISCLOSURE OF THE INVENTION

Problems to be Solved by the Invention

In the transient diffraction grating method according to the related art, in order to cross the two excitation light beams with the same wavelength to generate interfere fringes, the two excitation light beams having the optical path lengths are led to the area to be measured, and a probe light beam with a certain incident angle is incident on the diffraction grating formed by the generated interference fringes. It is thus necessary to cross the two excitation light beams and the one probe light beam at one point to be measured, and thus to adjust three optical axes of the excitation light beams and the probe light beam. Therefore, adjustment thereof becomes difficult.

As the excitation light beam used when molecules (particles) such as protein are used as the sample, it is necessary to employ a large laser light source with a short wavelength such as an excimer laser light source, and the size of the device thus increases.

Moreover, when the molecules (particles) such as protein are used as the sample, the protein molecules (particles) do not generally show changes in the refractive index, the absorption coefficient, and the diffusion coefficient due to the excitation light beams, and it is thus necessary to label the sample by a reagent (fluorescent reagent) which is to be photoexcited.

However, attributes and properties of the protein molecules (particles) to be measured may change due to the labeling of the sample.

Moreover, since the labeling is generally an irreversible reaction, the molecules (particles) in the sample may be destructed, the measurement cannot thus be repeated with the same sample, and the molecules (particles) cannot be recovered to be used for other purposes. Moreover, the photoexcitation used to form the transient diffraction grating is generally irreversible reaction. If a sample is once measured, the sample subsequently generates only a weak signal, which causes a problem in that the measurement cannot be repeated.

Moreover, when particles other than molecules such as protein which can be easily labeled are used as the sample, some materials may not be labeled, photoexcitation of the particles by the excitation light beam may be difficult, and the measurement by means of the above-described transient diffraction grating may be difficult.

The present invention is devised in view of the foregoing problems, and has a first object to provide an optical measuring device which can perform measurement using the transient diffraction grating method without using any excitation light beam and collimating two excitation light beams and a probe light beam.

Moreover, the present invention is to provide an optical measuring device which can measure characteristics with respect to diffusion of a sample by means of a transient diffraction without labeling the sample.

Meanwhile, in the dynamic scattering method (photon correlation method) of measuring fluctuation of scattered light from particles in order to measure nanoparticles, it is necessary to measure small fluctuation of large scattered light, that is, to measure a variation of the light intensity in bright field of view. In the principle of the dynamic scattering method, low measurement sensitivity and a bad S/N ratio are inevitable.

A second object of the invention is to provide a method and device capable of measuring the diameter of a nanoparticle with high sensitivity and a high S/N ratio as compared to the dynamic scattering method according to the related art.

Means for Solving the Problems

In order to attain the first object, according to an aspect of the invention, there is provided an optical measuring device including: a power supply; a container that stores a liquid sample or a gel sample; a pair of electrodes that generate, in a portion of the container, an electric force line distribution in which areas having high electric force line density and areas having low electric force line density are regularly arranged in response to a voltage applied; a dielectrophoresis control unit that controls the generation of a transient diffraction grating using dielectrophoresis of particles in the sample caused by applying the voltage to the pair of electrodes and a variation in the transient diffraction grating due to the diffusion of the particles in the sample according to a variation in the applied voltage; a light source emitting light to the transient diffraction grating; and a plurality of photodetectors detecting diffracted light generated by the transient diffraction grating. In the optical measuring device, the particles are evaluated on the basis of a variation in the intensity of the diffracted light generated by the transient diffraction grating.

According to the optical measuring device of the aspect of the invention, the voltage is applied to the pair of electrodes from the power supply, and the electric force line distribution, in which the areas having high electric force line density and the areas having low electric force line density are arranged regularly, occurs in the portion of the container. With this electric force line distribution, a dielectrophoresis action occurs in the liquid sample in the container or the particles contained in the gel sample, and then the movement of the particles occurs. That is, since the regularly arranged electric force line distribution occurs in the container by the arrangement of the pair of electrodes, the particles of the liquid sample or the particles of the gel sample are concentrated on the areas having high electric force line density due to the dielectrophoresis action. Accordingly, areas having high particle density and areas having low particle density are arranged regularly, and thus a transient diffraction grating is formed.

When the probe light from the light source is emitted to the transient diffraction grating, diffracted light is generated in a specific direction by the transient diffraction grating. When the transient diffraction grating is stably generated by the dielectrophoresis action, strong diffracted light is generated. In a state in which the transient diffraction grating is stably generated by voltage application, when a variation in the voltage application occurs, for example, the voltage application stops, the electric force lines are changed or disappear and accordingly the dielectrophoresis is changed or stops. For this reason, the particles in the container move by diffusion and thus the transient diffraction grating is broken to become gradually faint. As a result, the intensity of the diffracted light generated by the transient diffraction grating is decayed as time goes on. The decay curve at that time represents the diffusion coefficient. Therefore, it is possible to obtain information on the diffusion coefficient of the particles and the shape, the particle diameter, and the interaction with a solvent of each of the particles by measuring the intensity of the diffracted light by means of the photodetectors and obtaining the decay curve of the intensity of the diffracted light.

According to another aspect of the invention, there is provided an optical measuring method including: forming a transient diffraction grating by using a pair of electrodes that generate, in a portion of the container, an electric force line distribution in which areas having high electric force line density and areas having low electric force line density are regularly arranged in response to a voltage applied, and by applying the voltage to the electrode pair to cause dielectrophoresis of particles in a liquid sample; subsequently changing the applied voltage so as to diffuse the particles in the liquid sample forming a transient diffraction grating; and detecting a variation in the intensity of diffracted light generated by the transient diffraction grating to evaluate the particles.

According to the optical measuring method of another aspect of the invention, the voltage is applied to the electrode pair such that dielectrophoresis of particles in the liquid sample is caused and the particles in the liquid sample are concentrated in the areas having the high electric force line density, so that the transient diffraction grating is generated by the particles. Subsequently, the voltage is changed so as to diffuse the particles in the liquid sample forming the transient diffraction grating. Then, the transient diffraction grating is broken as time goes on. The particles are evaluated by detecting a variation in the intensity of the diffracted light according to the variation of the transient diffraction grating at that time.

In order to attain the second object, according to still another aspect, there is provided a nanoparticle measuring method including: causing a particle group to have a space-periodical concentration change by applying an electric field having a space period to a gel sample in which the particle group or particles are movably dispersed in a medium so as to form a pseudo diffraction grating; detecting diffracted light obtained by emitting light to the particle groups; and computing the particle diameter and the diffusion coefficient of the particle group from a time change of the diffracted light from the point of time when the application of the electric field is changed.

According to yet another aspect of the invention, there is provided a nanoparticle measuring device which uses the optical measuring method and includes: a sample storing unit storing a sample in which a particle group to be measured is movably dispersed in a medium or a gel sample in which the particle group to be measured is dispersed; electrodes and a power supply used to apply an electric field having a space period to the sample in the sample storing unit; a light source emitting light to the sample in the sample storing unit; a detection optical system detecting diffracted light generated by passing the light through the sample; and a data processing unit that computes the particle diameter and the diffusion coefficient of the particle group from a time change of the diffracted light from the point of time when the application of the electric field is changed in a state in which a space-periodical concentration change is generated in the particle group by applying the electric field.

In the nanoparticle measuring device according to this aspect, the sample storing unit is a transparent cell containing the sample, and the electrodes are transparent electrodes that are provided to the sample cell and include a plurality of portions extending in parallel to one another at predetermined intervals.

In the nanoparticles measuring method and device according to the aspects of the invention, the pseudo diffraction grating according to a variation in the spatial concentration of the particle groups is generated by applying the electric field to the particle groups that are in a diffused state in the medium. Then, the application of the electric field is changed while the diffracted light generated by the diffraction grating is detected. In this case, the particle diameter and the diffusion coefficient of the particle groups are computed from a variation in the diffracted light until the particle groups return to the diffused state. In this way, the object of the invention is attended.

That is, since the particle group diffused in the medium has a zeta potential, when the electric field having the space period to the particle group, the particle group moves in the medium in accordance with the electric field and thus the space-periodical concentration change occurs in the particle group, so that the diffraction grating is generated by the particle group. In this state, when the application of the electric field is changed, for example, when the application of the electric field stops, the particle group returns to the diffused state such that the concentration becomes uniform, which causes the diffraction grating to disappear. When the particles are small, the diffracted light disappears quickly, and when the particles are large, the diffracted light disappears slowly. When light is emitted to the particle group and then the diffracted light is detected from a time point when the diffraction grating is generated by the particle group to a time point when the diffraction grating disappears, it is possible to see the time it takes for the diffracted light to disappear. Further, it is possible to obtain the particle diameter and the diffusion coefficient of the particle group from the time it takes for the diffracted light to disappear by Expressions (2) and (3), which will be described below.

The diffracted light generated by emitting light to the pseudo diffraction grating generated by the particle group travels at an angle corresponding to the wavelength of the light passing through the particle group and the grating interval of the diffraction grating and is stronger than scattered light generated from individual particles by the dynamic scattering method. Therefore, the signal to be measured is strong, and the S/N ratio and the sensibility are remarkably improved, as compared to the dynamic scattering method.

In the nanoparticle measuring method according to this aspect of the invention, a transparent cell is used as the sample storing unit containing the sample in which the particle group is movably dispersed in the medium, and transparent electrodes, which are provided to the transparent cell, include a plurality of portions extending in parallel to one another at predetermined intervals, are used as the electrodes for applying the electric field to the sample, and have a refractive index approximate to the refractive index of the material of the transparent cell. This structure is preferable to reduce the effect of the electrodes on the diffracted light.

BRIEF DESCRIPTION OF THE DRAWINGS

FIG. 7A is a schematic front view of the sample cell 1 as seen in a laser beam radiation direction, and FIG. 7B is a schematic expanded sectional view taken along the line VIIB-VIIB shown in FIG. 7A.

FIG. 8 is a view illustrating the action of the nanoparticle measuring device according to the embodiment of the invention.

REFERENCE NUMERALS

Figure 1:
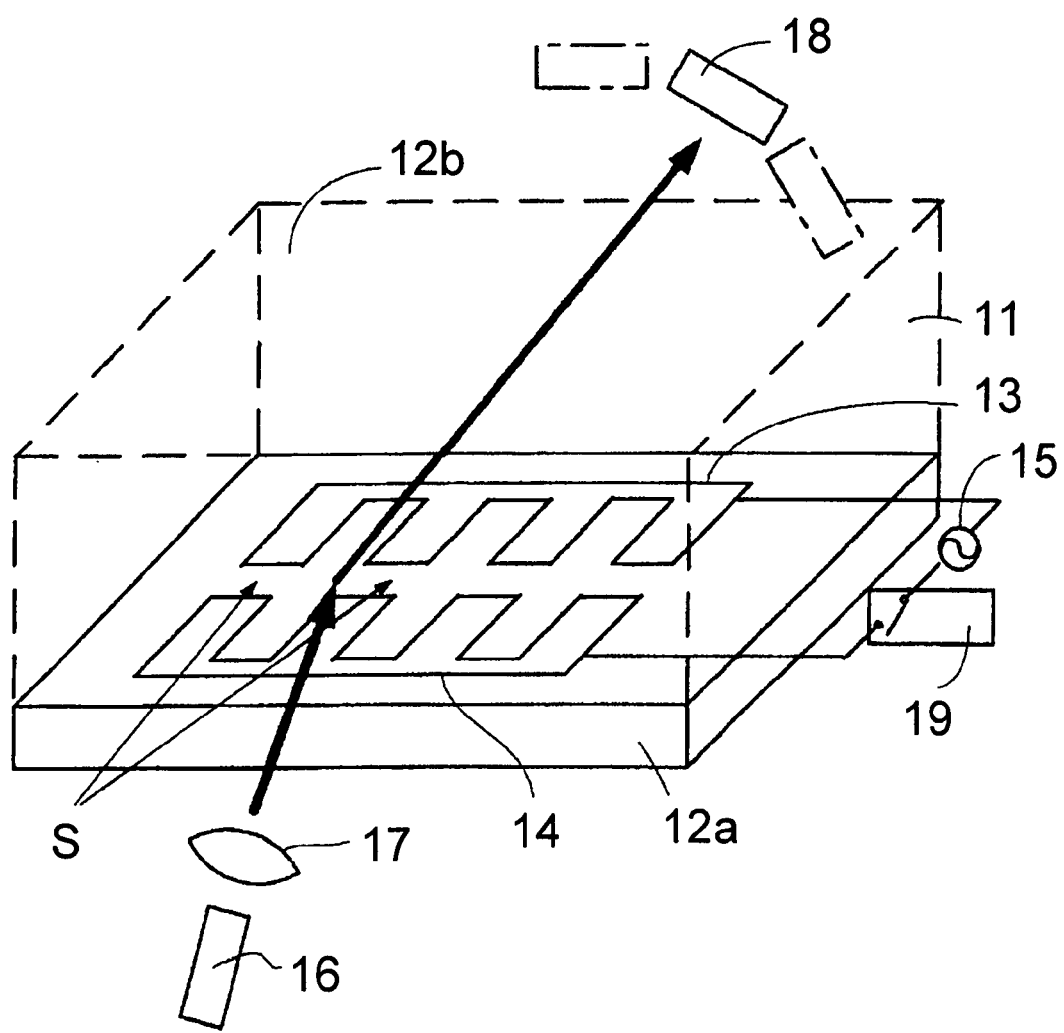
FIG. 1 is a perspective view illustrating the structure of an optical measuring device according to an embodiment of the invention.

11 Container
12a Bottom plate
12b Frame
13, 14 Electrodes
13a to 13d and 14a to 14d Linear electrode tooth
13e, 14e Connecting portion
15 AC power supply
16 Light source
17 Lens system
18 Photodetector
19 Dielectrophoresis control unit
21 Sample cell
31 Transparent glass
33 Transparent electrode 33a Finger portion
22 Electrode power supply
23 Laser beam source
24 Detection optical system
24a Pin hole
24b Photodiode
25 Beam stopper
26 Device control and data acquisition/processing device
P Particle
W Sample

BEST MODE FOR CARRYING OUT THE INVENTION

Hereinafter, embodiments of the invention will be described with reference to the accompanying drawings. It should be noted that the present invention is not limited to the following embodiments, and includes various forms without departing from the purpose of the present invention.

Figure 2:
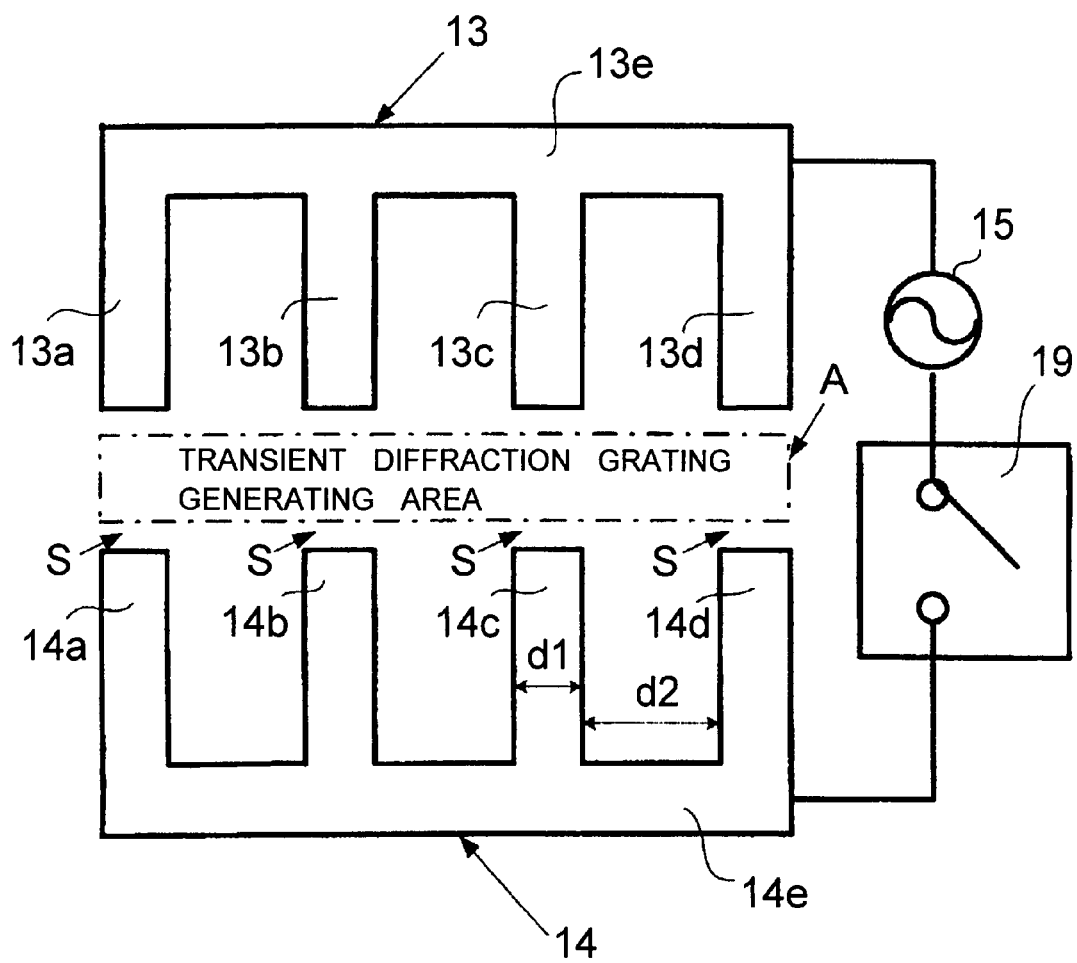
FIG. 2 is a plan view illustrating the shape of an electrode portion of the optical measuring device shown in FIG. 1.

FIG. 1 is a perspective view illustrating the structure of an optical measuring device according to an embodiment of the invention, and FIG. 2 is a plan view illustrating the structure of an electrode portion of the optical measuring device shown in FIG. 1. The optical measuring device performs optical measurement while using a dielectrophoresis action. The optical measuring device includes a container 11 that stores a liquid sample containing particles, a pair of electrodes 13 and 14 formed on a bottom surface 12a of the container 11, an AC power supply 15 that applies an AC voltage to the electrodes 13 and 14, a light source 16, a lens optical system 17 that converges light emitted from the light source, a plurality of photodetectors 18 that detect diffracted light, and a dielectrophoresis control unit 19 that controls a voltage applied from the AC power supply 15 to the electrodes 13 and 14.

A frame 12b is bonded on the bottom surface 12a to form side walls, thereby forming the container 11. In order for incident light to be capable of being radiated to a gap between the electrodes 13 and 14 through the bottom surface 12a, the container 11 is formed of a transmissive material, such as glass. Alternatively, the container except for a portion where incident light is radiated may be shielded from undesired light by using a material other than transmissive materials or providing a light shielding member, thereby increasing detection sensitivity.

The electrodes 13 and 14 are formed on the bottom surface 12a by using a mask patterning method. In this embodiment, the electrodes 13 and 14 are formed on the bottom surface 12a. However, when the container 11 is sufficiently deep, the electrodes 13 and 14 may be formed on the frame 12b forming the sidewalls, not on the bottom surface 12a.

The electrode 13 includes a plurality of linear electrode teeth 13a, 13b, 13c, and 13d that are arranged in parallel with each other at a constant interval and a connecting portion 13e electrically connecting one-side ends of those linear electrode teeth, thereby having a comb shape.

Similarly, the electrode 14 includes a plurality of linear electrode teeth 14a, 14b, 14c, and 14d that are arranged in parallel with each other at a constant interval and a connecting portion 14e electrically connecting one-side ends of those linear electrode teeth, thereby having a comb shape.

Further, the electrodes 13 and 14 are disposed such that the other-side ends of the linear electrode teeth 13a, 13b, 13c, and 13d face the other-side ends of the linear electrode teeth 14a, 14b, 14c, and 14d with predetermined gaps S, respectively.

It is preferable to set the electrode widths d1 of the individual linear electrode teeth to a predetermined dimension within a range of 0.5 μm to 20 μm and the intervals d2 between any two neighboring linear electrode teeth to a predetermined dimension within a range of 0.5 μm to 20 μm. However, the shapes or dimensions of the electrodes 13 and 14 are not particularly limited as long as the predetermined gaps S are disposed at a constant interval, and when a voltage is applied to the electrodes 13 and 14, an area with a high electric force line density is generated in each gap S and an area with a low electric force line density is generated next to the area with the high electric force line density. For example, the electrode width d1 and the interval d2 may be different from each other, and the shape of the electrode teeth may not be a line.

An AC power supply having a voltage and a frequency that can cause dielectrophoresis of particles is used as the AC power supply 15. More specifically, an AC power supply capable of applying an AC voltage having a level of 1 V to 100 V and a frequency of 10 KHz to 10 MHz is used. In general, it is preferable to use a high-frequency power supply.

Also, a kind of light source is selected as the light source 16 for generating the probe light beam to be radiated in accordance with a liquid sample to be measured. For example, it is preferable to use a HeNe laser beam source (whose wavelength is 633 nm) or other laser beam sources.

The lens optical system 17 focuses the light emitted from the light source, and the optical axis of the lens optical system 17 can be adjusted such that the light emitted from the light source is radiated to an area A where a transient diffraction grating including the gaps S between the electrodes 13 and 14 is formed. Also, it is preferable that the incident angle of the light emitted from the light source be adjusted such that both transmitted diffracted light and reflected diffracted light are obtained in accordance with a measurement subject and a measurement purpose. For example, when measurement is performed by means of transmitted diffracted light, the incident angle is set to satisfy a condition under which total reflection does not occur at the interface between the bottom surface of the container and the liquid sample.

The photodetectors 18 are disposed upside the liquid sample to detect the transmitted diffracted light. Each photodetector 18 is provided with an angle adjusting mechanism for measuring a diffraction angle so as to be capable of detecting the diffraction angle and the intensity of the diffracted light. A photodiode or a CCD is used as the photodetector 18. Instead of the angle adjusting mechanism, an array sensor in which a plurality of elements are arranged may be used to measure the diffraction angle.

The dielectrophoresis control unit 19 is composed of a computer including a CPU, a ROM, a RAM, and so on, and controls the AC power supply 15 to apply a required AC voltage to the electrodes 13 and 14 for the time required to form a transient diffraction grating and then to stop the voltage application, thereby diffusing the particles.

Next, the measuring operation of the optical measuring device will be described. In advance, the optical system is adjusted such that light from the light source 16 can be incident on the area A.

Figure 3:
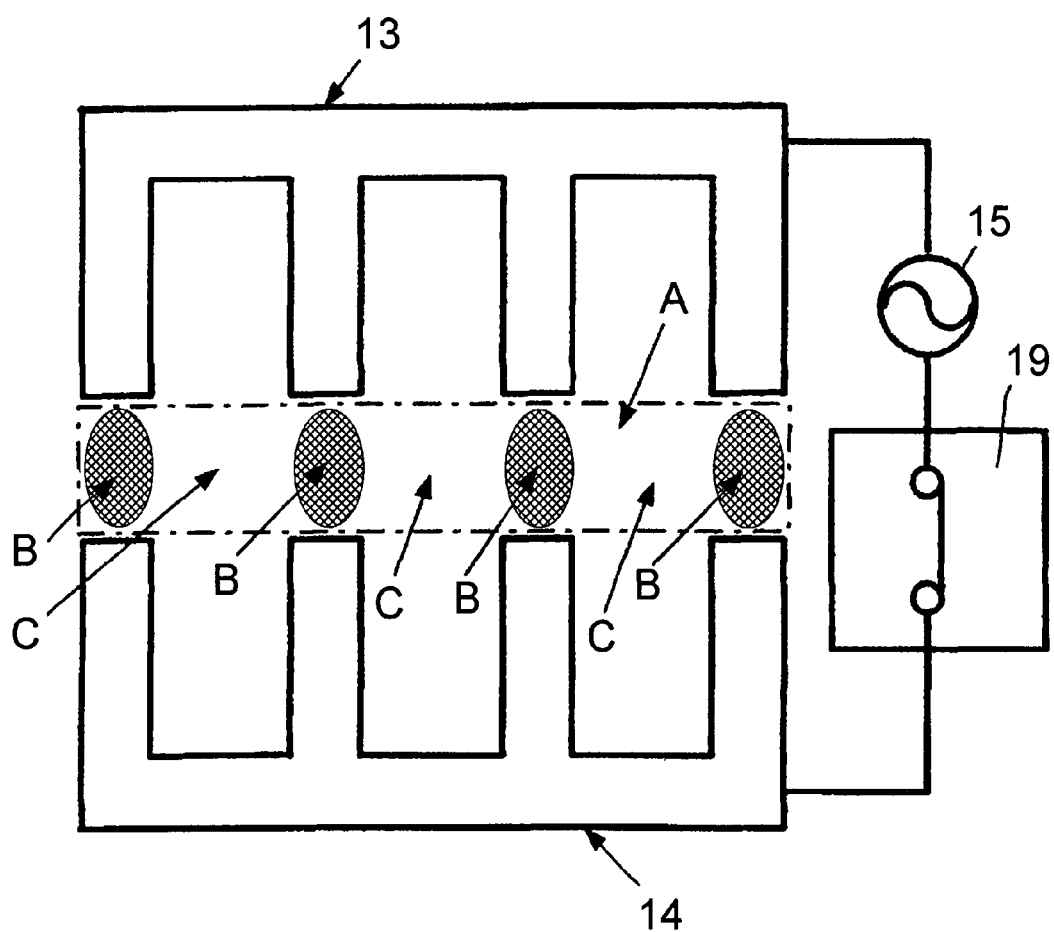
FIG. 3 is a view illustrating a transient diffraction grating generated when an AC voltage is applied to electrodes.

First, the dielectrophoresis control unit 19 controls the AC power supply 15 to apply an AC voltage $V_0$ to the electrodes 13 and 14. When particles (of, for example, protein) are present in a liquid sample, due to dielectrophoresis action caused by the AC voltage, the particles move into areas where electric force line is concentrated. FIG. 3 is a view illustrating the state of the particles when the AC voltage is applied. Since the particles move into the portions of the gaps S where the electric force line is concentrated, as shown in FIG. 3, areas B with dense particles and areas C with sparse particles are alternately arranged, thereby forming a transient diffraction grating by the particles.

At this time, the light from the light source 16 incident on the area A is diffracted in a predetermined direction by the transient diffraction grating. When the AC voltage is continuously applied, the transient diffraction grating stably exists and thus the diffracted light whose intensity is strong is detected by the photodetectors 18. The intensity of the diffracted light is measured as a reference value.

Figure 4:
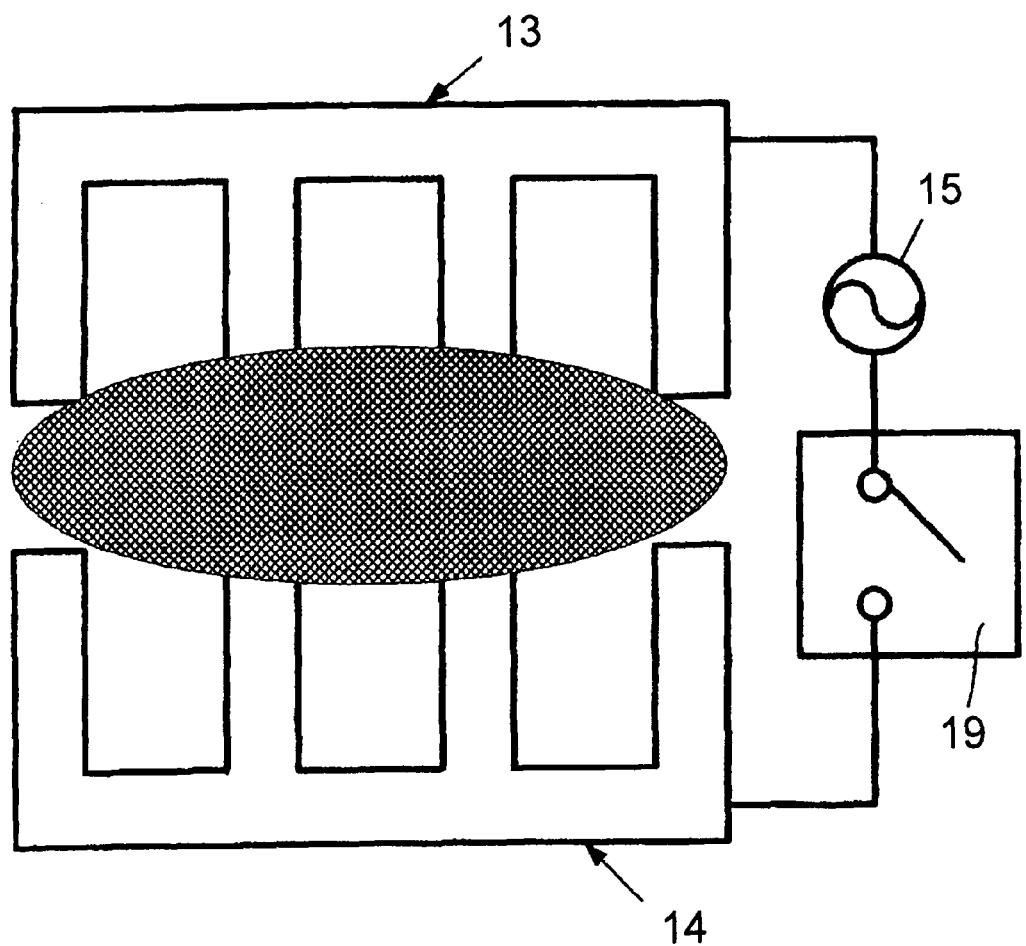
FIG. 4 is a view illustrating a state of when voltage application stops after the transient diffraction grating is formed so as to diffuse particles.

Subsequently, the dielectrophoresis control unit 19 controls the AC power supply to stop the application of the AC voltage to the electrodes 13 and 14. Then, the dielectrophoresis action stops and thus the particles concentrated on the gaps S are diffused so as to gradually spread. As a result, the transient diffraction grating is broken to become gradually faint and is finally extinguished as shown in FIG. 4. In the course when the transient diffraction grating becomes faint, the intensity of the diffracted light becomes weak, and the variation in the intensity of the diffracted light is measured by the photodetectors 18.

Figure 5:
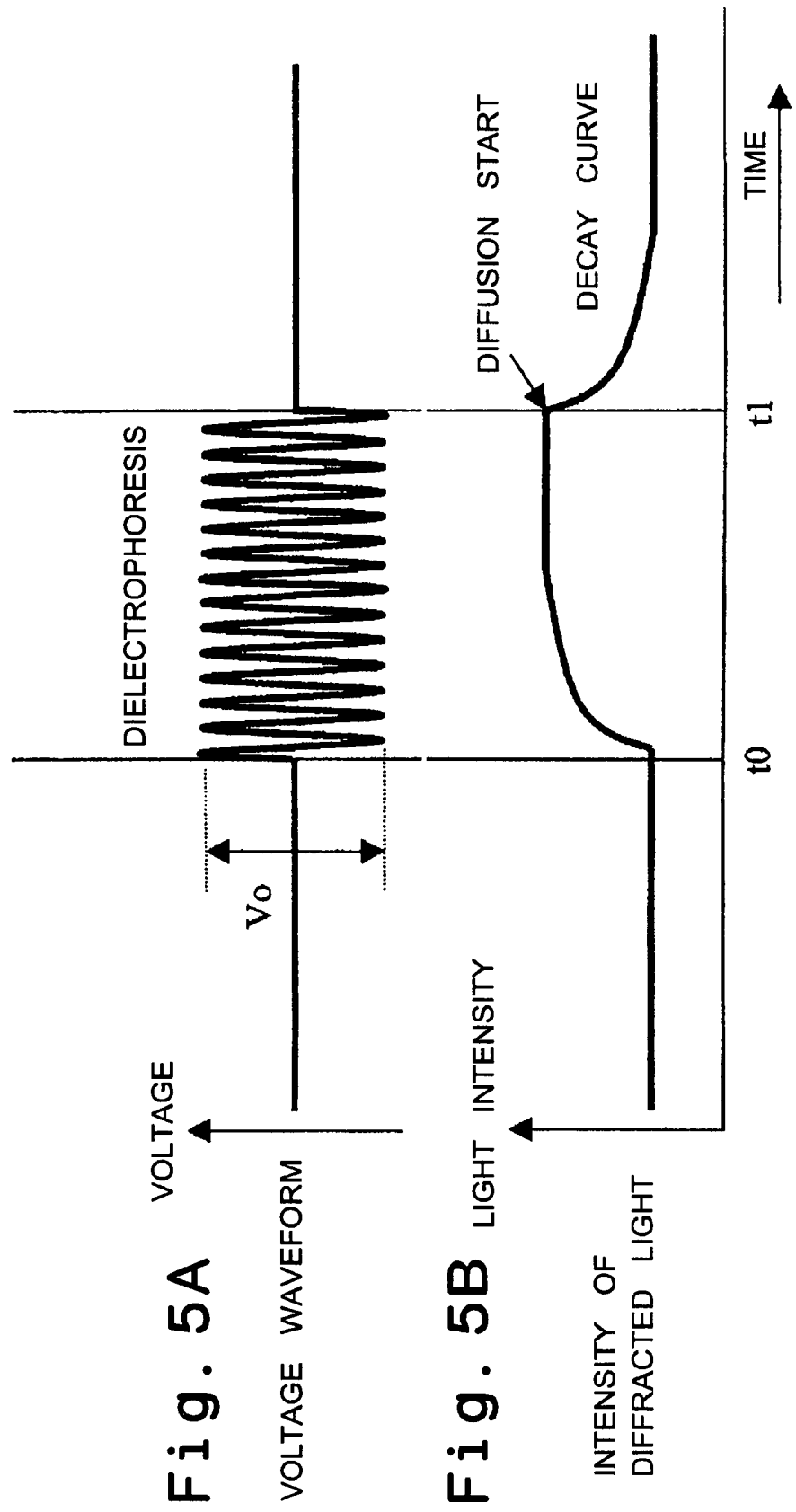
FIG. 5 is a timing chart illustrating an application voltage waveform (A) and the intensity of diffracted light (B) in the optical measuring device according to the embodiment of the invention.

FIG. 5 shows a timing chart with respect to the variation in the intensity of the diffracted light obtained in the above-mentioned measuring operation together with the waveform of the applied voltage. A decay curve after the dielectrophoresis stops depends on a diffusion coefficient. Therefore, it is possible to obtain information on the diffusion of the particles by obtaining the diffusion coefficient from the decay curve.

Other Embodiments

In the above-mentioned embodiment, the transmitted diffracted light is detected. However, the reflected diffracted light may be detected. Even when the liquid sample has a light absorbing property, the use of the reflected diffracted light makes it possible to easily detect the diffracted light.

An optical measuring device for measuring reflected diffracted light has the same structure as that shown in FIG. 1 except that the photodetectors 18 are disposed below the bottom surface 12a.

When reflected diffracted light is measured, preferably, the incident angle of the light emitted from the light source 16 is adjusted to satisfy a condition that total reflection occurs so as to increase the amount of reflected diffracted light as much as possible. For example, when the container 11 is made of glass and an aquatic sample is stored in the container 11 as the liquid sample, it is preferable to set the incident angle to about 46°.

Further, in the above-mentioned embodiment, the electrodes 13 and 14 are disposed such that the one-side ends of the linear electrode teeth of the electrode 13 face the one-side ends of the linear electrode teeth of the electrode 14, so that the transient diffraction grating is formed in the gap between the electrodes. However, the shape pattern of the electrodes is not limited thereto. In conclusion, any shape, which can cause areas with a high electric force line density and areas with a low electric force line density to be alternately and regularly arranged when a voltage is applied, so as to form a transient diffraction grating by dielectrophoresis, can be used to realize this invention.

Furthermore, in the above-mentioned embodiment, an example in which the liquid sample containing the dispersed particles is measured has been described. However, it is also possible to measure a gel sample containing particles dispersed therein. Also, even when a DC voltage is applied instead of the AC voltage, it is possible to perform the same measurement as described above. In addition, in the above-mentioned embodiment, an example in which the application of the voltage stops after the transient diffraction grating is formed such that the particles spread has been described. However, instead of stopping the application of the voltage, it is possible to change a voltage applied. For example, when an AC voltage is used, it is possible to spread particles by changing the period or amplitude of the AC voltage.

Next, a nanoparticle measuring device according an embodiment of the invention will be described.

Figure 6:
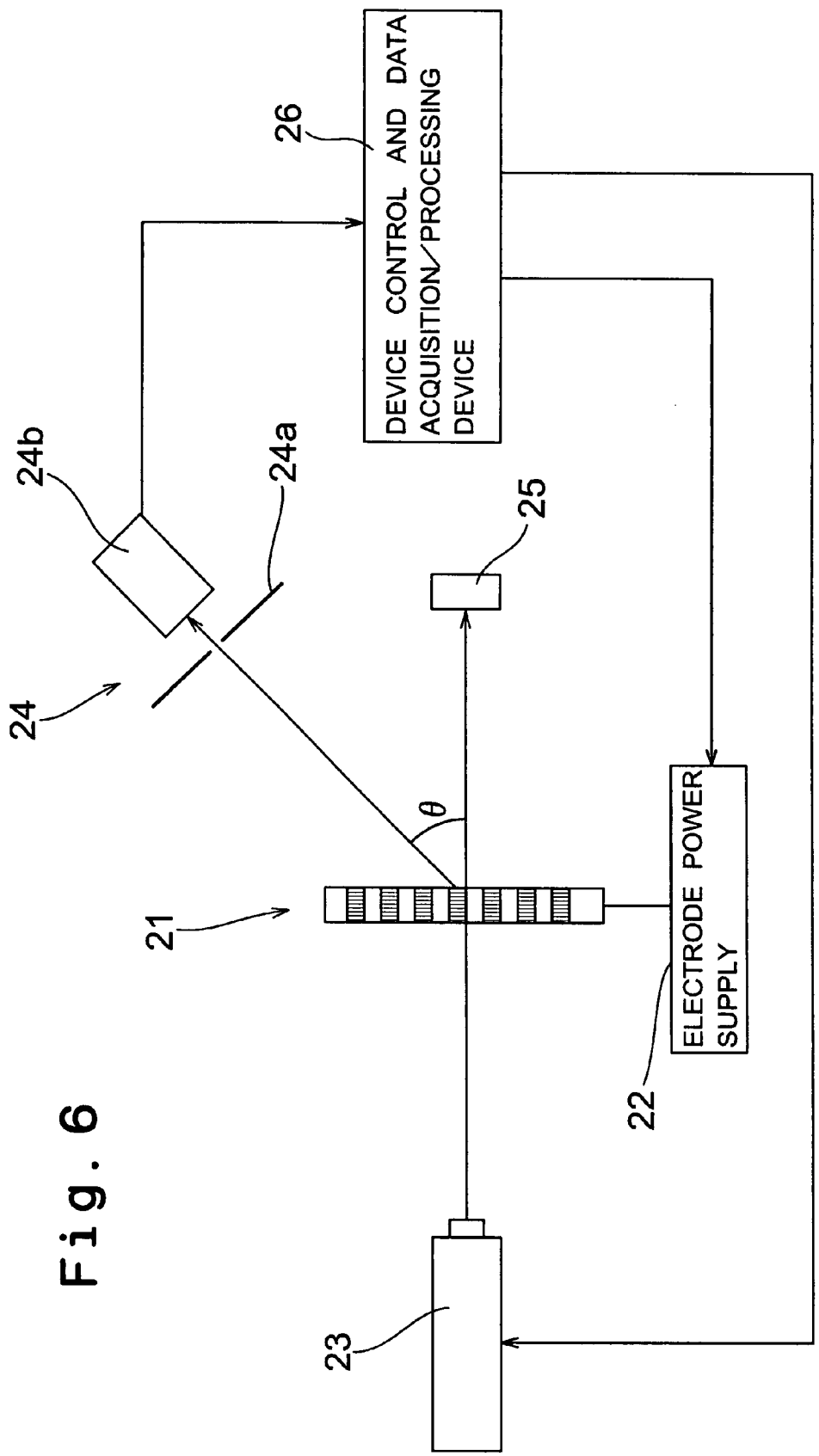
FIG. 6 is a view illustrating the structure of a nanoparticle measuring device according to an embodiment of the invention, more specifically, a view illustrating a schematic diagram showing the optical structure of the nanoparticle measuring device and a block diagram the electrical structure of the nanoparticle measuring device.
Figure 7A:
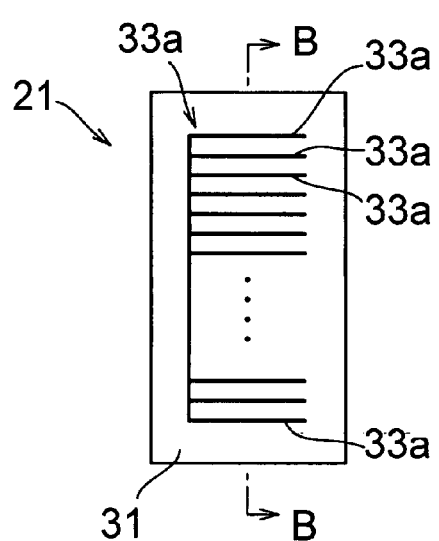
FIGS. 7A and 7B are views for explaining the structure of a sample cell 21 shown in FIG. 6, and more specifically.
Figure 7B:
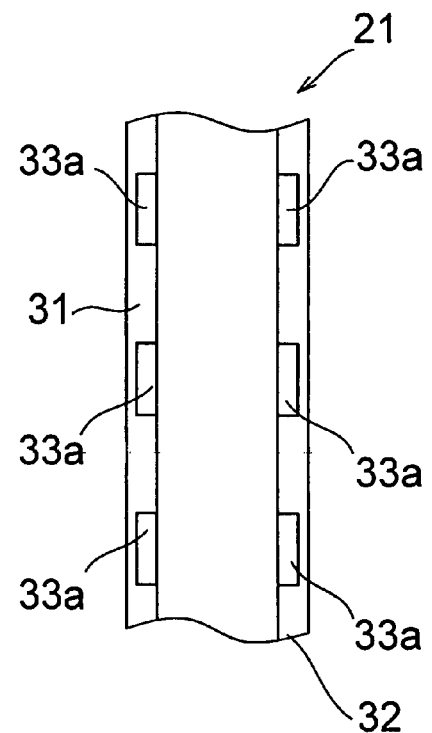

FIG. 6 is a view illustrating the structure of a nanoparticle measuring device according to an embodiment of the invention. More specifically, FIG. 6 is a schematic diagram showing the optical structure of the nanoparticle measuring device and a block diagram showing the electrical structure of the nanoparticle measuring device. FIGS. 7A and 7B are views for explaining the structure of a sample cell 21 shown in FIG. 6. More specifically, FIG. 7A is a schematic front view of the sample cell 21 as seen in a laser beam radiation direction, and FIG. 7B is a schematic expanded sectional view taken along the line VIIB-VIIB shown in FIG. 7A.

The sample cell 21 includes two transparent glass substrates 31 and 32, which face each other in parallel with a minute gap therebetween, as portions of peripheral walls. During usage, those transparent glass substrates 31 and 32 are disposed in a vertical direction. On the transparent glass substrates 31 and 32, comb-shaped transparent electrodes 33 are mounted at positions facing each other and each of the comb-shaped transparent electrodes 33 has a plurality of finger portions 33a arranged with a constant gap $\Delta$ along the vertical direction and extending in a horizontal direction. An electrode power supply 22 selectively supplies a positive or negative voltage to the transparent electrodes 33. When a voltage is supplied to the transparent electrodes 33, an electric field having a space period based on the pattern of the finger portions 33a is applied to a sample in the sample cell 21. For example, ITO can be used as the material of the transparent electrodes 33. The refractive index of ITO is about 2.0 and the transparent glass substrate 31 of the sample cell 21 is made of glass having a high refractive index of about 2.0 (for example, s-LAH79 (trade name) with a refractive index of 2.0 made by OHARA INC.), which is preferable in that, when a laser beam (which will be described below) is radiated, the laser beam is substantially diffracted by the transparent electrodes 33.

A laser beam from a laser beam source 23 is substantially horizontally radiated to the sample cell 21 from the transparent glass substrate 31. A detection optical system 24 for detecting the diffracted beam of the laser beam passing through the sample cell 21, which will be described below, is disposed on the side of the sample cell 21 opposite to the laser beam source 23. The detection optical system 24 is disposed at a position in a direction at an angle θ with respect to an optical axis L of the laser beam from the laser beam source 23, and is composed of a beam hole 24a and a photodiode 24b. Further, a beam stopper 25 for preventing the laser beam having passed through the sample cell 21 from leaking to, for example, the detection optical system 24 or the outside is provided on the optical axis L of the laser beam.

The diffracted light detected by the photodiode 24b is input to the device control and data acquisition/processing device 26 so as to be used to compute a particle diameter and a diffusion coefficient of a particle group to be measured by an operation, which will be described. The device control and data acquisition/processing device 26 performs the control of all devices in addition to the above-mentioned data processing and may be composed of, for example, a personal computer and peripherals connected the personal computer.

Next, a measuring operation of the embodiment of the invention having the above-mentioned structure and the principle thereof will be described.

The sample cell 21 is filled with a sample made by dispersing nanoparticle groups to be measured in a medium, such as water. In general, the surface of a nanoparticle dispersed in a liquid has a positive or negative surface potential (zeta potential). That is, the surface of a nanoparticle dispersed in a liquid is charged. A voltage having the same polarity as charges of the particles is applied to the above-mentioned transparent electrodes 33. For example, when the particles have positive charges, a positive voltage is applied to the transparent electrodes 33. In this case, when the zeta potentials of the particles are low, the surface potentials can be adjusted by means of, for example, a method of changing the PH of a medium liquid or a dispersing agent (surface active agent).

As shown in (A) of FIG. 8, when particles P to be measured in a sample W have positive charges, a positive voltage is applied to the electrodes 33. Then, the individual particles P repulse against the individual finger portions 33a of the electrodes 33 by a coulomb force so as to move to between the finger portions 33a of the electrodes 33 (electrophoresis), as shown in (B) of FIG. 8, so that a pseudo diffraction grating having a space period based on the pattern of the finger portions 33a is generated by the plurality of particles P. A laser beam, which is radiated to the sample cell 1 at that state, is diffracted by the plurality of particles P. If the distance between two adjacent finger portions 33a is Δ as described above, the wavelength of the laser beam is λ, a diffraction angle is θ, and an order is m, the following relationship is established:

$$m\lambda = \Delta \cdot \sin\theta \quad (1).$$

For example, when λ is 0.6328 μm and the distance Δ between two adjacent finger portions 33a is 3 μm, a first-order diffracted light appears at a diffraction angle θ of about 12°. The detection optical system 24 is disposed at the position in the direction at the angle θ with respect to the optical axis L of the laser beam and detects the intensity of the first diffracted light.

In a state in which the pseudo diffraction grating has been generated by the voltage applied to the sample as shown in (B) of FIG. 8, when the application of the voltage to the transparent electrodes 33 stops to eliminate the electric field, the individual particles P return to a diffused state as shown in (C) of FIG. 8. As the particles P are diffused, the pseudo diffraction grating disappears and the diffracted light is also eliminated. Since the period from the time point when the electrical field is eliminated to the time point when the diffracted light is eliminated depends on the diffusion time of the particles, it is possible to compute the diffusion coefficient D of the particles by measuring the elimination time of the diffracted light, which will be described in detail later.

Figure 9:
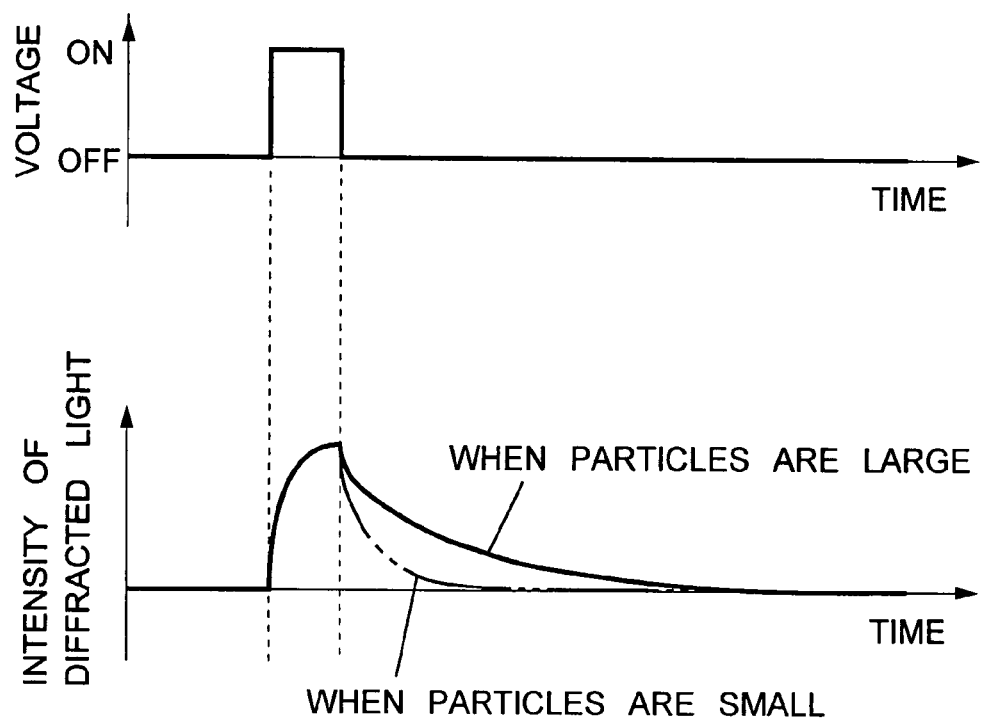
FIG. 9 is a graph illustrating the relationship between the intensity of the diffracted light and the ON/OFF timing of the voltage applied to the transparent electrodes 13 in the nanoparticle measuring device according to the embodiment of the invention.

FIG. 9 is a graph illustrating the relationship between the intensity of the diffracted light and the ON/OFF timing of the voltage applied to the transparent electrodes 33. When the diameter of each of the particles is large, the period from the time point when the electrical field is eliminated to the time point when the particles P are diffused such that the diffraction grating disappears becomes long. In contrast, when the diameter of each of the particles P is small, the period becomes short.

A variation in the concentration of the particles P due to diffusion is expressed by the following diffusion equation 1.

[Equation 1]

$$\frac{\partial u(x,t)}{\partial t} = div[Dglad\{u(x,t)\}] \quad (2)$$

Here, u(x,t) represents a particle concentration, x represents a spatial coordinate in a direction along which the gaps d are formed among the finger portions 33a, and t represents time.

A variation in the intensity of the diffracted light according to the variation in the concentration of the particles is obtained in advance and a variation in the intensity of the diffracted light over time is detected. Then, it is possible to compute the diffusion coefficient D of the particles P by using Expression (2).

The relationship between the diffusion coefficient D and the particle diameter d is expressed by the following Einstein-Stokes relational equation.

[Equation 2]

$$D = \frac{kT}{3\pi\mu_0 d} \quad (3)$$

The device control and data acquisition/processing device 26 can exactly measure the time it takes for the diffracted light to disappear by synchronizing timings when the intensity of the diffracted light is sampled with the timings when the voltage applied to the electrodes 33 is turned on and off, can compute the diffusion coefficient D from Expression (2) by using the measured result, and can compute the diameter d of the particle P from Expression (3) by using the diffusion coefficient D.

An especially notable point of the above-mentioned embodiment is that a signal for obtaining the diffusion coefficient D and the particle diameter d is not a signal obtained by measuring fluctuation of light scattered by the individual particles, unlike the dynamic scattering method according to the related art, but a signal obtained by measuring the light diffracted by the pseudo diffraction grating formed by the plurality of particle groups. Therefore, the sensitivity and the S/N ratio are remarkably improved as compared to the dynamic scattering method.

In the above-mentioned embodiment, the diffracted light may be generated due to the difference between the diffraction index of the transparent glass sheets 31 and 32 of the sample cell 21 and the diffraction index of the transparent electrodes 33. In this case, the intensity of the diffracted light is detected by the detection optical system 24. However, since the diffracted light is not changed over time, the diffracted light does not affect the measurement by subtracting the intensity of the diffracted light having no change from the whole intensity of the diffracted light after the measurement.

Figure 10:
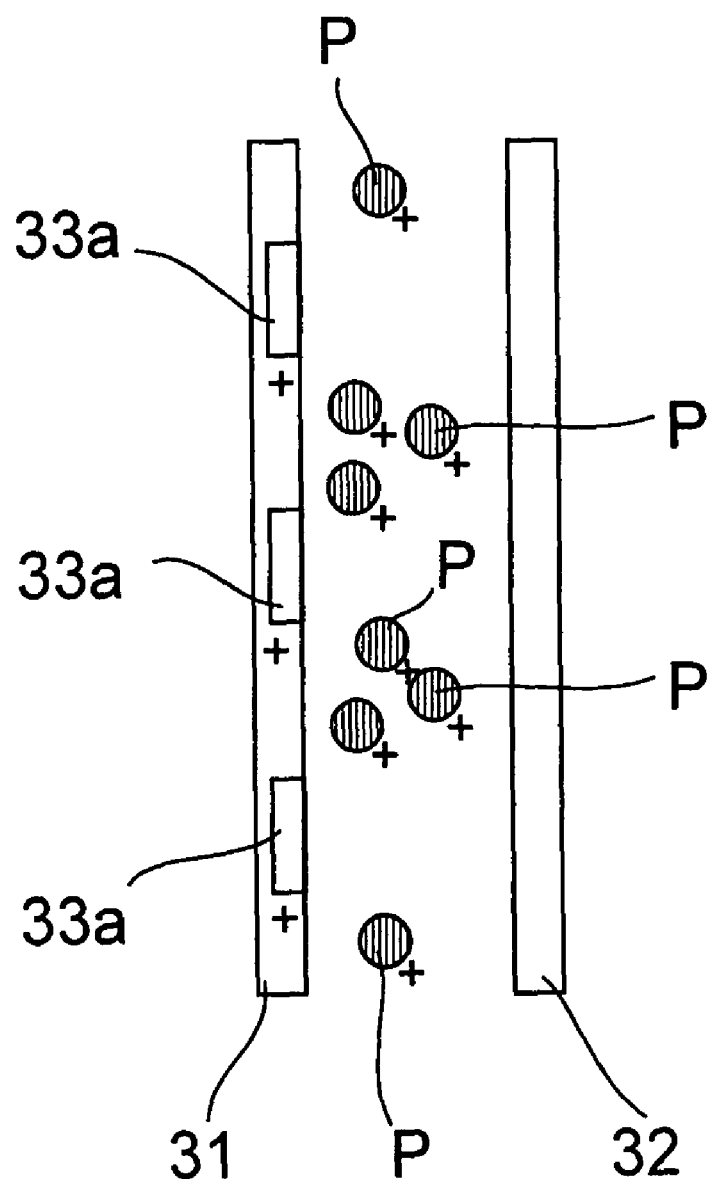
FIG. 10 is a view illustrating an example of an electrode structure of a sample cell of a nanoparticle measuring device according to another embodiment of the invention.

Further, in the above-mentioned embodiment, an example in which the transparent electrodes 33 are mounted on the transparent glass sheets 31 and 32, facing each other, of the sample cell 21 to face each other has been described. However, as shown in FIG. 10, it is possible to provide a transparent electrode having a plurality of finger portions 33a as the above example on only one of the two transparent glass sheets 31 and 32 facing each other. Even in this case, when a voltage is applied to the individual finger portions 33a, the particles P form a pseudo diffraction grating as the above example.

Figure 11:
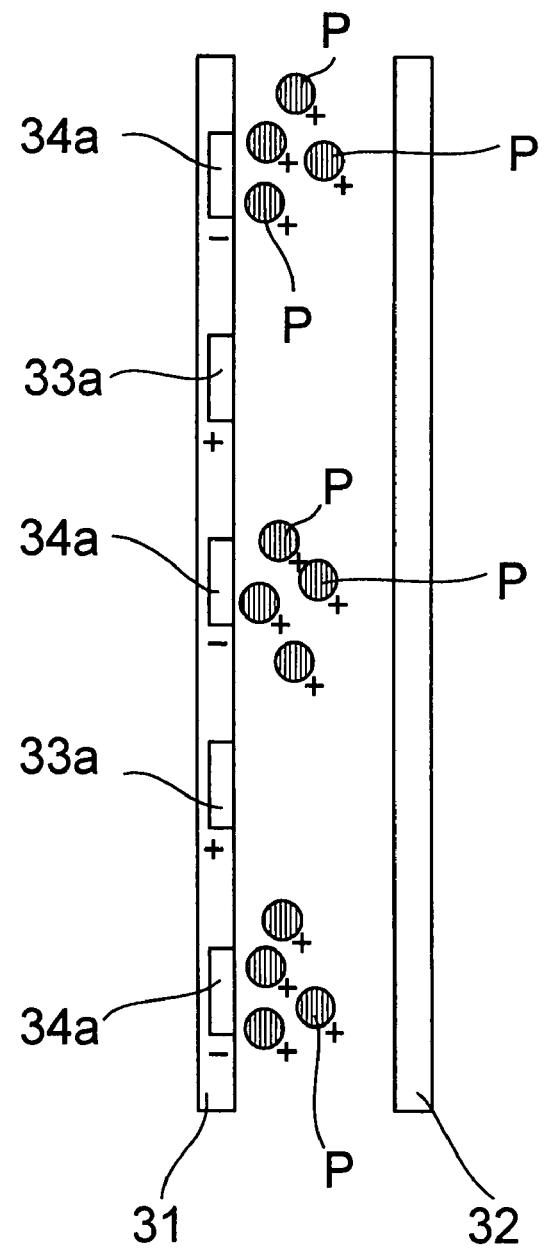
FIG. 11 is a view illustrating an example of the electrode structure of a sample cell of a nanoparticle measuring device according to still another embodiment of the invention.
Figure 12:
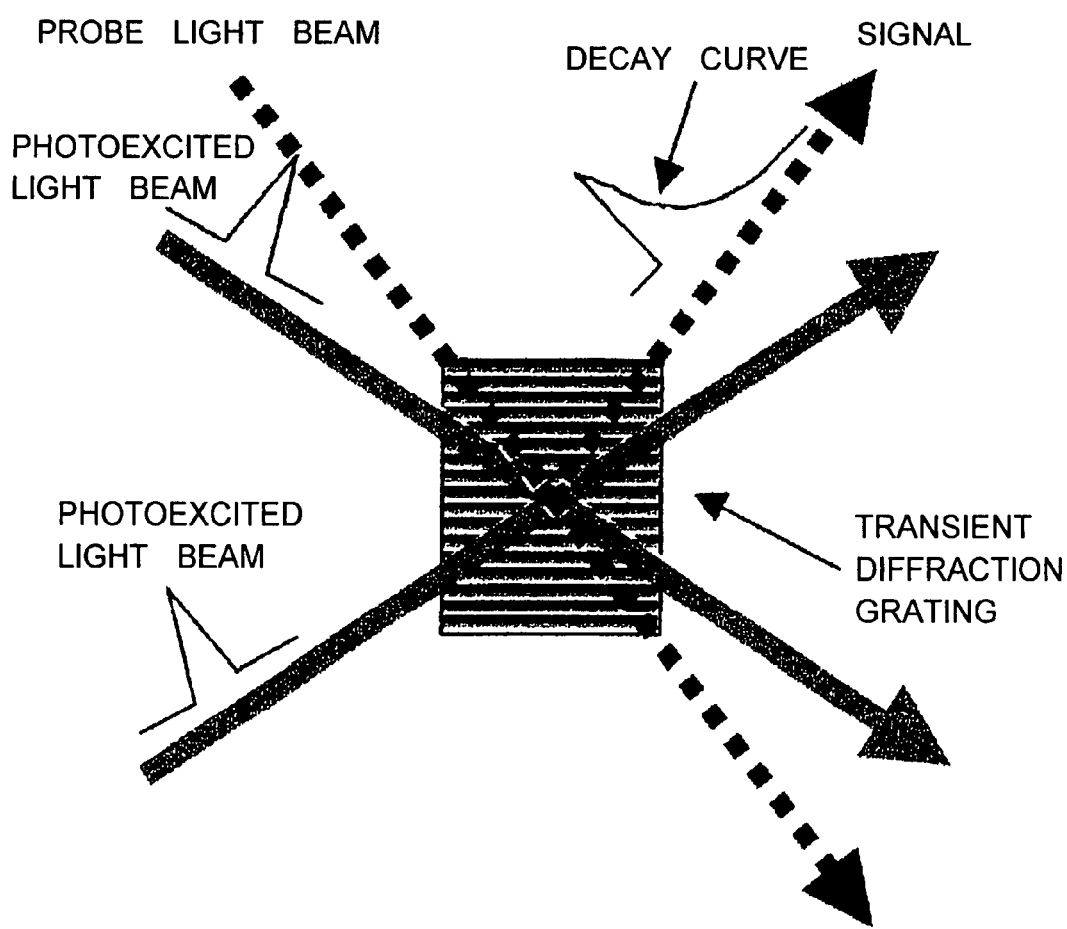
FIG. 12 is a view illustrating a transient diffraction grating method according to the related art.

Further, as shown in FIG. 11, it is possible to use an electrode structure in which a transparent electrode having a plurality of finger portions 33a as the above example and a transparent electrode having a plurality of finger portions 34a are mounted on at least one of the transparent glass sheets 31 and 32 such that the finger electrodes 33a and 34a are alternately arranged, and voltages having opposite polarities are applied to the transparent electrodes, respectively. In this case, for example, positively-charged particles P moves along the finger electrodes 34a to which a negative voltage is being applied, thereby forming a pseudo diffraction grating. The grating interval of the diffraction grating formed by the particle groups becomes two times as wide as the grating interval of the diffraction grating formed by the finger electrodes 33a and 34a and thus light diffracted by the particle groups and light diffracted by the electrodes have different diffraction angles. Therefore, it is possible to reduce the effect of the electrodes on the diffracted light.

Furthermore, in the above-mentioned embodiment, an example in which groups of particles to be measured dispersed in a medium liquid has been described. However, gas may be used as a medium, in addition to a liquid. Also, there are some kinds of particles that are movably dispersed in a solid. In this case, a solid is used as the medium. Similarly, it is possible to perform measuring on a gel sample in which particles are dispersed.

Also, in the above-mentioned embodiment, the laser beam is radiated to the diffraction grating formed by the particles and the diffracted light of the laser beam is measured. However, light other than a laser beam may be radiated. Also, after forming the pseudo diffraction grating by the particle, instead of stopping the application of the voltage to the electrodes, for example, it is possible to decrease a voltage applied such that the particles are spread.

INDUSTRIAL APPLICABILITY

With the optical measuring device according to the embodiment of the invention, it is possible to form a transient diffraction grating without using excitation light. Therefore, it is possible to easily perform optical measurement of biomolecules, such as protein, or various minute particles using the transient diffraction grating by adjusting an optical axis of probe light to a measurement position. With the optical measuring device and method according to the embodiments of the invention, it is possible to measure the characteristics, such as the diffusivity of the sample by using the transient diffraction grating without labeling the sample and without light excitation. Therefore, it is possible to remeasure the sample and to reuse the sample.

Further, in the optical measuring device according to the embodiment of the invention, when each of the electrodes making a pair includes the plurality of electrode teeth arranged at a constant interval and the connecting portion electrically connecting one-side ends of those electrode teeth, and the pair of electrodes are disposed such that the other-side ends of the electrode teeth of one electrode face the other-side ends of the electrode teeth of the other electrode with predetermined gaps, respectively, the areas with the high electric force line density are concentrated at the positions of the gaps with which the other-side ends of the electrode teeth of the one electrode face the other-side ends of the electrode teeth of the other electrode and the areas with the low electric force line density are concentrated in the areas neighboring the areas with the high electric force line density, so that the transient diffraction grating is generated along the gaps with which the other-side ends of the electrode teeth of the one electrode face the other-side ends of the electrode teeth of the other electrode. Therefore, the transient diffraction grating is generated in an area where the pair of electrodes does not exist (the gaps between the facing electrodes). As a result, it is possible to measure a variation in the intensity of the diffracted light that is affected not by the pair of electrodes but by only the transient diffraction grating.

In the nanoparticle measuring method and device according to the embodiments of the invention, it is possible to measure nanoparticles with a relatively simple device structure. Further, since the intensity of a signal to be detected remarkably increase as compared to the dynamic scattering method according to the related art, it is possible to improve the sensitivity and the S/N ratio.

Furthermore, since a structure in which a sample obtained by dispersing particle groups to be measured in a medium is stored in the transparent cell and an electric field having a space period is applied by the transparent electrodes provided to the transparent cell is used, it is possible to reduce the effect of the electrodes on the diffracted light.

The invention claimed is:

1. An optical measuring device comprising:
a power supply;
a container that stores a liquid sample or a gel sample;
a pair of electrodes that generate, in a portion of the container, an electric force line distribution in which areas having high electric force line density and areas having low electric force line density are regularly arranged in response to a voltage applied;
a dielectrophoresis control unit that controls the generation of a transient diffraction grating using dielectrophoresis of particles in the sample caused by applying the voltage to the pair of electrodes and a variation in the transient diffraction grating due to the diffusion of the particles in the sample according to a variation in the applied voltage;
a light source emitting light to the transient diffraction grating; and
a plurality of photodetectors detecting diffracted light generated by the transient diffraction grating,
wherein the particles are evaluated on the basis of a variation in the intensity of the diffracted light generated by the transient diffraction grating.

2. The optical measuring device according to claim 1, wherein the power supply is an AC power supply.

3. The optical measuring device according to claim 1, wherein the variation in the applied voltage after the generation of the transient diffraction grating is to stop voltage supply.

4. The optical measuring device according to claim 1, wherein each of the electrodes making the pair includes a plurality of electrode teeth arranged at a constant interval and a connecting portion electrically connecting the electrode teeth, and
one-side ends of the electrode teeth of one of the electrodes are disposed to face one-side ends of the electrode teeth of the other electrode with gaps therebetween.

5. The optical measuring device according to claim 1, wherein at least a portion of the container is formed of a material transmitting light from the light source, the electrode pair is formed in the portion of the container transmitting the light from the light source, the light from the light source is incident on the portion of the container toward the transient diffraction grating, and the photodetectors detect diffracted light having passed through the sample or diffracted light reflected from the sample.

6. An optical measuring method comprising:
forming a transient diffraction grating by using a pair of electrodes that generate, in a portion of a container, an electric force line distribution in which areas having high electric force line density and areas having low electric force line density are regularly arranged in response to a voltage applied, and by applying the voltage to the electrode pair to cause dielectrophoresis of particles in a sample;

subsequently changing the applied voltage so as to diffuse the particles in the sample forming a transient diffraction grating; and detecting a variation in the intensity of diffracted light generated by the transient diffraction grating to evaluate the particles.

7. The optical measuring method according to claim 6, wherein the variation in the applied voltage after the generation of the transient diffraction grating is to stop voltage application.

8. A nanoparticle measuring method comprising:

causing a particle group to have a space-periodical concentration change by applying an electric field having a space period to a gel sample in which the particle group or particles are movably dispersed in a medium so as to form a pseudo diffraction grating;

detecting diffracted light obtained by emitting light to the particle groups; and computing the particle diameter and the diffusion coefficient of the particle group from a time change of the diffracted light from the point of time when the application of the electric field is changed.

9. The nanoparticle measuring method according to claim 8, wherein the light is a laser beam.

10. The nanoparticle measuring method according to claim 8, wherein the variation in the electric field after the generation of the pseudo diffraction grating is to stop the application of the electric field.

11. A nanoparticle measuring device comprising:
a sample storing unit storing a sample in which a particle group to be measured is movably dispersed in a medium or a gel sample in which the particle group to be measured is dispersed; electrodes and a power supply used to apply an electric field having a space period to the sample in the sample storing unit; a light source emitting light to the sample in the sample storing unit; a detection optical system detecting diffracted light generated by passing the light through the sample; and a data processing unit that computes the particle diameter and the diffusion coefficient of the particle group from a time change of the diffracted light from the point of time when the application of the electric field is changed in a state in which a space-periodical concentration change is generated in the particle group by applying the electric field to the sample so as to form a pseudo diffraction grating.

12. The nanoparticle measuring device according to claim 11, wherein the light is a laser beam.

13. The nanoparticle measuring device according to claim 11, wherein the variation in the electric field after a space-periodical concentration change is generated in the particle group is to stop the application of the electric field.

14. The nanoparticle measuring device according to claim 11, wherein the sample storing unit is a transparent cell for containing the sample, and the electrodes are transparent electrodes that are provided to the sample cell and include a plurality of portions extending in parallel to one another at predetermined intervals.

* * * * *